(12) United States Patent
Reid

(10) Patent No.: US 7,698,152 B2
(45) Date of Patent: Apr. 13, 2010

(54) MEDICAL IMAGE VIEWING MANAGEMENT AND STATUS SYSTEM

(75) Inventor: Frank Reid, Downingtown, PA (US)

(73) Assignee: Siemens Medical Solutions Health Services Corporation, Malvern, PA (US)

(*) Notice: Subject to any disclaimer, the term of this patent is extended or adjusted under 35 U.S.C. 154(b) by 834 days.

(21) Appl. No.: 11/269,478

(22) Filed: Nov. 8, 2005

(65) Prior Publication Data
US 2006/0155579 A1 Jul. 13, 2006

Related U.S. Application Data

(60) Provisional application No. 60/641,963, filed on Jan. 7, 2005.

(51) Int. Cl.
G06Q 10/00 (2006.01)
G06Q 50/00 (2006.01)

(52) U.S. Cl. ........................................................ 705/2

(58) Field of Classification Search .................. 705/2, 705/4; 250/583; 395/203; 378/4; 382/128, 382/239; 345/356, 473; 358/473
See application file for complete search history.

(56) References Cited

U.S. PATENT DOCUMENTS

| | | | |
|---|---|---|---|
| 4,553,206 A | 11/1985 | Smutek et al. | |
| 4,833,625 A | 5/1989 | Fisher | |
| 5,605,153 A | 2/1997 | Fujioka et al. | |
| 5,737,539 A * | 4/1998 | Edelson et al. | 705/3 |
| 6,181,342 B1 * | 1/2001 | Niblack | 345/635 |
| 6,396,500 B1 * | 5/2002 | Qureshi et al. | 345/473 |
| 6,441,927 B1 * | 8/2002 | Dow et al. | 358/473 |
| 6,603,494 B1 * | 8/2003 | Banks et al. | 715/807 |
| 6,735,272 B1 * | 5/2004 | Sorenson | 378/4 |
| 6,972,425 B2 * | 12/2005 | Tamakoshi et al. | 250/583 |
| 7,099,490 B1 * | 8/2006 | Fujita et al. | 382/100 |
| 7,130,474 B2 * | 10/2006 | Luo et al. | 382/239 |
| 7,272,263 B2 * | 9/2007 | Okada | 382/233 |
| 7,321,673 B2 * | 1/2008 | Watai et al. | 382/128 |

* cited by examiner

*Primary Examiner*—Gerald J. O'Connor
*Assistant Examiner*—John A Pauls
(74) *Attorney, Agent, or Firm*—Alexander J Burke

(57) ABSTRACT

A system identifies, flags and tracks images and series of images previously accessed by a healthcare worker. A system for tracking medical image viewing by a user includes at least one repository storing data representing multiple medical images of a particular patient available for use in preparing a report. A viewing processor tracks whether an individual image of the multiple medical images has been presented on a display device by using predetermined rules in determining whether data representing the individual image has been communicated to the display device for display to a particular user associated with received user identification information. The viewing processor generates a viewed indicator associated with the individual image and the particular user in response to a determination data representing the individual display image has been communicated to the display device for display to the particular user. A documentation processor at least one of, (a) associates data representing the generated viewed indicator with data representing the individual image and (b) stores data, representing the generated viewed indicator and associates the generated viewed indicator with the individual image and the particular user, in a record.

17 Claims, 4 Drawing Sheets

MEDICAL IMAGE VIEWING MANAGEMENT AND STATUS SYSTEM

This is a non-provisional application of provisional application Ser. No. 60/641,963 by F. Reid filed Jan. 7, 2005.

FIELD OF THE INVENTION

This invention concerns a system for tracking and documenting the communication and viewing of medical data such as medical images of a particular patient by a user, for example.

BACKGROUND OF THE INVENTION

In Hospitals or other patient treatment facilities, medical imaging systems such as MRI, CT scan, X-ray and Ultrasound systems are employed by radiology and other hospital departments. Such medical imaging systems are often integrated with, or are in communication with, a Radiology Information System (RIS) used within a radiology department. Radiologists typically use a RIS or other system in acquiring medical images of a particular patient for review on a workstation and for the preparation of a report to be communicated to another treating physician, clinician or the patient. However, in the course of treatment of a patient, it is occasionally desirable to determine whether medical images or reports concerning a particular patient have been generated or reviewed by a particular user such as a physician, clinician, nurse or even the patient. This may occur, for example, during an audit of medical procedures to establish procedures are being correctly carried out, or to resolve a question of a healthcare worker over whether images have been reviewed or need to be scheduled for physician review or to verify particular healthcare workers are correctly performing their duties. It may also occur in the context of a medical malpractice investigation. Existing RIS and other systems fail to provide such a capability. A system according to invention principles addresses these deficiencies and associated problems.

SUMMARY OF THE INVENTION

A system identifies, flags and tracks images and series of images read and analyzed by a healthcare worker in creating a report using a visual indicator identifying images that are used or not used for the report and documents characteristics concerning image importation and viewing on a report generation workstation. A system for tracking medical image viewing by a user includes at least one repository storing data representing multiple medical images of a particular patient available for use in preparing a report. A viewing processor tracks whether an individual image of the multiple medical images has been presented on a display device by using predetermined rules in determining whether data representing the individual image has been communicated to the display device for display to a particular user associated with received user identification information. The viewing processor generates a viewed indicator associated with the individual image and the particular user in response to a determination data representing the individual display image has been communicated to the display device for display to the particular user. A documentation processor at least one of, (a) associates data representing the generated viewed indicator with data representing the individual image and (b) stores data, representing the generated viewed indicator and associates the generated viewed indicator with the individual image and the particular user, in a record.

DETAILED DESCRIPTION OF THE INVENTION

Figure 1:
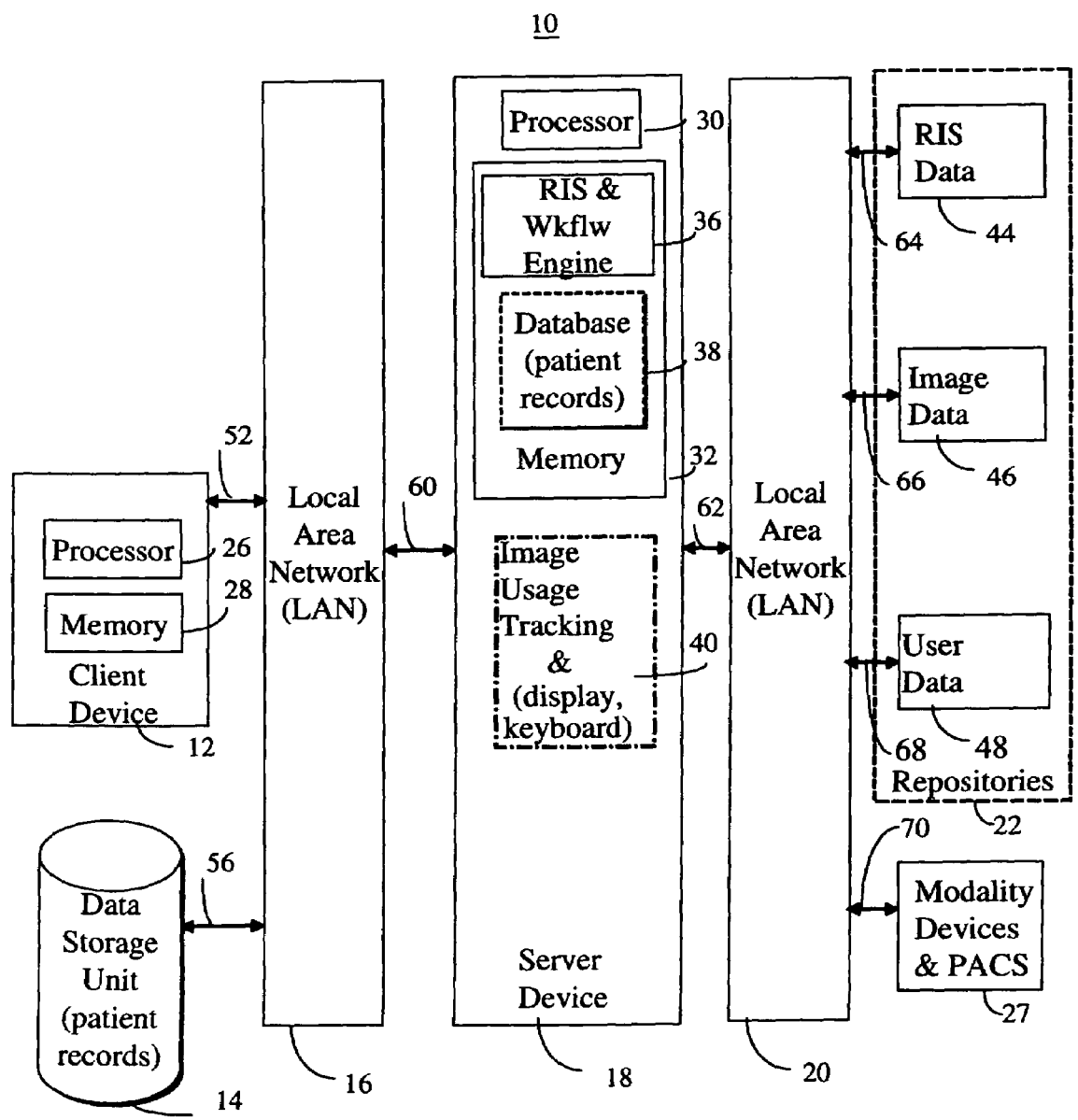
FIG. 1 shows a networked radiology information system including an image usage tracking and documentation system and user interface, according to invention principles.

FIG. 1 shows a networked radiology information system including an image usage tracking and documentation system and user interface. The image usage tracking system identifies, flags and tracks images read and analyzed by a radiologist to create a report. The system appends data representing a visual indicator (e.g., a visual cue or an icon) to an individual image object which comprises an image series and individual images of a particular patient. The visual indicator associated with individual image objects allows a radiologist to identify images that were used or not used for a report. Additionally a healthcare worker that displays the images of the particular patient may readily see which images have been used (e.g., previously reviewed for a report) or not used. In another feature, the image usage tracking system incorporates an audit system, including a log file manager and operates in the background of a radiology information system (RIS) application. The audit system creates and maintains audit records that document those images that are imported to an image review and report generation workstation. The audit records identify, a particular user accessing particular medical data and images of a particular patient. The audit system also documents image usage characteristics including, how long an image was displayed and if any features related to anatomical condition or function of the anatomical part shown in the image were applied to the image. The audit system stores audit records in a log file that is stored with data representing an image object so that it can be readily accessed and produced as required.

The system advantageously enables a radiologist to prove that he analyzed particular image data of a particular patient on a particular date and time. This capability is of value in the event of a medical malpractice investigation initiated by a patient alleging a diagnostic mistake, for example. Existing systems fail to provide a radiologist with a method to verify that the images produced by an imaging modality of a particular patient were in fact used and viewed as part of the creation of a report. Existing standards and methods support comparison and verification of a number of images acquired from an imaging modality versus the number of images stored. However existing system fail to enable determination of whether or not an image appeared on a viewing monitor of a diagnostic workstation for a radiologist to view and analyze.

The system enables a radiologist to determine that all images of a diagnostic image study appeared on a viewing workstation at least once without requiring the radiologist to peruse extensive image lists derived from log file records identifying access by a particular user of particular images. The system facilitates this by providing an easy to interpret visual indicator identifying that images have appeared on the viewing screen at least once. This further enables the radiologist to safely finalize a radiological report. The system is usable by radiologists and other healthcare professionals who prepare and verify a medical report of any type and advantageously increases the quality of a diagnosis performed by a radiologist by ensuring that a full complement of images generated in a patient examination has been viewed and are part of a resultant report. In response to a radiologist completing a report and viewing all of the images of a diagnostic study without ignoring images, the system stores data flags or log file data indicating access to image data. This stored information is evidence that medical images have been at least displayed on a radiology workstation and consequently there is a likelihood that they have been appropriately considered by a radiologist, for example.

An executable application as used herein comprises code or machine readable instruction for implementing predetermined functions including those of an operating system, healthcare information system or other information processing system, for example, in response user command or input. An executable procedure is a segment of code (machine readable instruction), sub-routine, or other distinct section of code or portion of an executable application for performing one or more particular processes and may include performing operations on received input parameters (or in response to received input parameters) and provide resulting output parameters. A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device.

FIG. 1 shows a networked radiology information system 10 incorporating an image usage tracking and documentation system and user interface 40. System 40 also includes a PACS-RIS viewer application as part of the user interface supporting viewing of images within a RIS (Radiology Information System) or PACS (Picture Archiving and communication System). Radiology information system 10 includes a client device 12, a data storage unit 14, a first local area network (LAN) 16, a server device 18, a second local area network (LAN) 20, repositories 22 and modality devices and PACS system 27 including imaging and radiological treatment devices. Repositories 22 may comprise one repository (e.g., a database) or multiple repositories. The client device 12, e.g., a radiology image viewing or other workstation, includes processor 26 and memory unit 28 and may comprise a personal computer, for example. The Radiology information system 10 is used by a healthcare provider that is responsible for providing radiological services within a hospital or as a separate facility. Although the system is described in the context of a radiology department, this is exemplary only. The system is also applicable in other hospital departments (e.g. cardiology, etc.). Examples of healthcare providers include, without imitation, a hospital, a nursing home, an assisted living care arrangement, a home health care arrangement, a hospice arrangement, a critical care arrangement, a health care clinic, a physical therapy clinic, a chiropractic clinic, and a dental office. Examples of the people being serviced by the healthcare provider include, without limitation, a patient, a resident, and a client.

Server device 18 includes image usage tracking and documentation system and user interface 40, processor 30, a memory unit 32 including RIS and workflow system 36 and a database 38 containing patient records including medical data identifying treatments previously received by a patient. RIS and workflow system 36 derives schedule data identifying current and future types of radiological imaging procedures and duties being performed by particular healthcare workers or that are scheduled to be performed by particular workers. Image usage tracking and documentation system 40 (which may also reside in client device 12) includes an input device that permits a user to perform data and command entry and input information and an output device that provides a user a display image showing a medical report including normal or near-normal results. The system 40 input device is a keyboard and mouse and also includes an automatic voice recognition and transcription unit and may also include a touch screen or a microphone, or a telephone voice response system for example. The output device comprises a display but may also be a printer or speaker, for example. The output device provides information to the user responsive to the input device receiving information from the user or responsive to other activity by client device 12. For example, a display presents information responsive to the user entering information via a keyboard.

Image usage tracking and documentation system 40 automatically identifies, flags and tracks images and series of images read and analyzed by a healthcare worker in creating a report using a visual indicator identifying images that are used or not used for the report based on predetermined rules and instruction stored in memory 32. Image usage tracking system 40 also documents characteristics concerning image importation and viewing on a report generation workstation. System 40 acquires and collates patient medical information and RIS information from repositories 22 (which may comprise one or more databases, for example) and from imaging modalities (MRI, CT scan, X-ray, Ultrasound etc.) 27. Repositories 22 include, repository 44 containing RIS information (e.g., characteristics concerning a radiological imaging procedure radiation dose, image orientation, physician performing a procedure, equipment used etc.) and repository 46 including patient specific image data including image usage characteristics previously described. Repositories 22 also include, repository 48 containing user data (healthcare worker identifiers, credentials, roles, patient lists, locations etc.) and electronic and physical address and message information.

Figure 2:
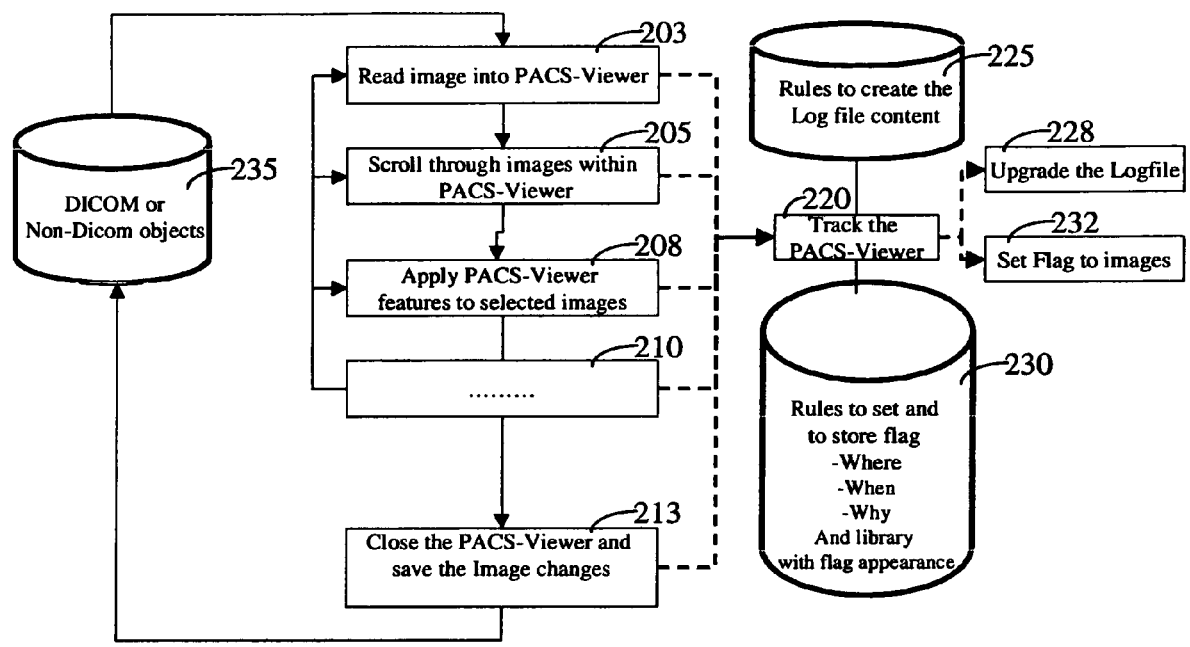
FIG. 2 shows a flowchart of a process and workflow used in processing image representative data, according to invention principles.

FIG. 2 shows a flowchart of a process and workflow used in processing image representative data employed by the networked radiology information system 10 of FIG. 1. In step 203, a user employing system 40 initiates access and viewing on workstation 12 of images in DICOM or non-DICOM compatible format from repository 235 which may comprise a repository in modality 27 or image repository 46, or a patient record database such as database 14 or 38. System 40 in step 205 provides one or more display images on workstation 12 enabling a user to scroll through and select particular accessed images. System 40 in step 208 enables a user to apply features related to anatomical condition or function of an anatomical part shown in one or more selected images. Such features include, for example, measurement values, anatomical feature indicators, anatomical operation characteristics such as vital signs, fluid volume or respiratory volume or fluid pump rates. Additional workflow steps involved in image review and annotation for the preparation and generation of a report, for example, are also supported by user interface display images provided by system 40 in step 210. A user completes an image review and annotation session and stores processed image data in DICOM or non-DICOM compatible format in repository 235 and initiates close of the session in step 213. An image usage tracking processor 220 in system 40 monitors image usage steps 203, 205, 208, 210 and 213 performed by a particular user. The particular user is identified by system 40 through user entered and pre-stored information including, for example, userid, password, authorization codes and user credentials.

Tracking processor 220 automatically monitors image usage steps 203, 205, 208, 210 and 213 and tracks individual images being accessed and displayed on workstation 12 using predetermined rules in repository 230. Tracking processor 220 determines whether data representing an individual image has been communicated to workstation 12 for display to a particular user associated with received user identification information. Tracking processor 220 in step 232 generates a viewed indicator associated with the individual image and the particular user in response to a determination data representing the individual display image has been communicated to workstation 12 for display to the particular user. The generated viewed indicator indicates that an associated individual image, image series, or group of images produced during an imaging procedure, had been accessed on workstation 12 during preparation of an imaging report or upon signoff (signifying completion) of either report preparation or an imaging review process. The generated viewed indicator is displayed on a DICOM compatible image, for example, or in a display screen associated with the image in response to the image being shown to a physician during a report preparation process in the form of a flag, icon, symbol or text attribute. The generated viewed indicator is an attribute that is stored as an attribute of a (two-dimensional or three-dimensional) image. Data representing a generated viewed indicator may be part of a DICOM compatible Object such as a Header-Attribute or may comprise, for example, a new DICOM Attribute, an overlaid DICOM-Pixel image or a DICOM Presentation State.

A different type of viewed indicator may be generated in response to the application of corresponding different rules in repository 230. The type of generated viewed indicator or one or more attributes of the viewed indicator, may also indicate, when, where, for how long and who accessed and downloaded an image as well as a displayed resolution of the image and a reason for which the image was accessed. The type of generated viewed indicator or one or more attributes of the viewed indicator, may also indicate, in which context the image was accessed and may identify image usage characteristics that were applied to the image.

A documentation processor in tracking processor 40, under direction of rules and instruction in repository 225, associates in step 228, data representing the generated viewed indicator with data representing the individual image and with an identifier of the particular user accessing the individual image, in a stored record (such as a log file) in a repository. The record is stored together with the image data in repository 235, e.g., in memory 32, but may also be stored in other repositories such as image repository 46, or patient record database such as database 14. Rules repositories 225 and 230 may also be stored in memory 32 or image repository 46, or a patient record database such as database 14, for example. The documentation processor records data comprising attributes of a generated viewed indicator in the log file indicating a workflow (sequence of tasks) performed by a radiologist employing image usage tracking system 40.

The documentation processor stores data in the log file identifying images accessed by a particular user and how an individual image is processed during imaging report preparation. Specifically, the data stored in the log file also identifies when, where, for how long and who accessed and downloaded an image as well as a displayed resolution of the image and a reason for which the image was accessed. The data stored in the log file also records data indicating a context in which the image was accessed and identifies image usage characteristics that were applied to the image. The data stored in the log file further records data identifying patient anatomical images that are concurrently displayed in a composite image and also records which images are two-dimensional, three-dimensional and those that are video clips, together with imaging Procedure identifier, image Series identifier, individual Image identifier and data indicating the time at which an image or series of images is displayed or accessed.

The documentation processor in tracking processor 220 records data in the log file comprising attributes of a generated viewed indicator received from a PACS-RIS executable application in unit 40, unit 36 or modality 27. The viewed images are identified by identifiers in the log file as the images are not stored in the log file. Records stored within the Log file are created in the background concurrently with operation of the PACS-RIS application. A user identifier stored in the log file is determined from a user entered password or wirelessly by user specific RFID tag, or via biometric identification (finger, iris, voice print) for example. A unique identifier is assigned to a log file that is generated during imaging report preparation and supports storage and archiving of the log file in repository 235 (FIG. 2). The unique identifier may also be assigned to a log file upon sign off or completion of either, an imaging review or report generation process. The unique identifier assigned to a log file allows association of a log file to a corresponding imaging report.

The log file record may advantageously comprise a DICOM object stored with images of an imaging procedure. A variety of different formats may be used for a created log file including HL7, XML or DICOM, for example. Further, the unit 220 documentation processor includes an authorization processor governing user access to a log file. An administrator or system manager may configure authorization and allow access to a log file by selected users. A PACS-RIS Viewer application in system 40 employs a log file to reconstruct a complete imaging report preparation process by identifying images accessed and mouse clicks and other user commands made during an imaging report preparation process.

Tracking processor 220 advantageously generates and associates a viewed indicator with both individual images and groups of images such a DICOM compatible image series or other image series of a diagnostic study, portion of a study or of an imaging procedure that are accessed and displayed on workstation 12. An image series viewed indicator and image procedure viewed indicator are shown in a RIS user interface or a browser on workstation 12 that is used for accessing an image series or images of an imaging procedure. Tracking processor 220 automatically generates and associates a viewed indicator with both individual images and groups of images under the direction of predetermined rules and instruction in repository 230. The predetermined rules and instruction in repository 230 include multiple different rules governing when tracking processor 220 automatically generates and associates a viewed indicator with an image or group of images. Specifically, tracking processor 220 automatically generates and associates a viewed indicator with an image or group of images when, (a) an image or group of images is selected or modified by a user on workstation 12 and (b) a selected proportion of data representing image content is downloaded from server 18 or modality 27 and shown on the display of workstation 12.

Download of image representative data for presentation by an image viewer on workstation 12 occurs in a progressive manner so that, for example, a proportion such as ten percent of the content images of a selected series are downloaded and appear firstly on workstation 12 via a PACS-RIS Viewer application. The image quality (dependent on proportion of image content downloaded) increases as download continues. Subsequently, the images of the selected series appear with a substantial proportion of their quality enabling report generation. A user is able to choose images which need to be displayed with the highest quality and that are to be download and displayed first by selecting particular images or holding particular images in a display area using user interface menu controls.

The predetermined rules and instruction in repository 230 determine when a viewed indicator is to be generated and associated with an individual accessed image or group of images. Specifically, rules and instruction in repository 230 initiate tracking processor 220 to generate a viewed indicator for association with an image series of a diagnostic study or with an image series associated with a particular imaging procedure in response to data representing substantially all, or a predetermined portion of images of an image series being downloaded to workstation 12 for display processing, for example. Similarly, rules and instruction in repository 230 initiate tracking processor 220 to generate a viewed indicator for association with a particular image in response to substantially all, or a predetermined portion of the data representing a particular image being downloaded to workstation 12 for display processing, for example. A proportion of an individual image downloaded is determined by an estimate or measurement of a number of downloaded bytes as a proportion of a total number of bytes comprising the individual image, for example. In an alternative embodiment, the predetermined rules and instruction in repository 230 direct tracking processor 220 to generate a viewed indicator for association with a particular image in response to the particular image being presented on a display screen with a predetermined minimum resolution for more than a predetermined amount of time, for example. Other rules may also be employed in repository 230. In addition, system 40 supports user creation of rules in repository 230 and identifies and tracks particular rules in repository 230 during an imaging report preparation process. The system 40 user interface provides one or more images enabling a user to determine rules incorporated in repository 230 for generating a viewed indicator as well as rules for log file audit record generation incorporated in repository 225.

Existing systems use flags within a PACS, to identify images that are referenced within medical report descriptions. However, existing methods of documentation are largely manual and are readily manipulated by users to hide a mistake of a physician or hide procedural or other irregularities. These existing methods do not provide an authentic record of images accessed by a particular user for use for legal or other purposes requiring accurate verifiable traceable audited records. Further, in existing systems, if a radiologist attempts to ensure all images of a patient diagnostic study are viewed by systematically opening these images manually, there is no system to document that the images were in fact viewed and used in a report.

In contrast, image usage tracking system 40 validates that a radiologist accessed and viewed images and other clinical data used in preparing a medical report such as an imaging report concerning a patient procedure and promotes conscientious diagnosis. System 40 also provides records usable for legal purposes and minimizes manipulation of system records. The system 40 generation of image viewed indicators and storage of audit data in a log file may be optional (or permanent) features available on a PACS (Picture Archiving and Communication System) Workstation, or other image viewing and analysis system.

In an example of system operation, two image views of a patient chest comprising a PA view and a lateral view are accessed and viewed on workstation 12. These are single images belonging to the same study or procedure. Once the images have appeared on workstation 12, system 40 generates a viewed indicator (e.g., an icon) and appends the indicators to the displayed viewed images and a documentation processor records data in the log file indicating generated viewed indicators are associated with the viewed images. As a radiologist advances through each image derived by an imaging procedure, the generation of viewed indicators is repeated. Once all images of the imaging procedure have been viewed, a viewed indicator (e.g., an icon) is associated with the imaging procedure and is placed on a procedure level tab of a navigation image window. The radiologist dictates an imaging report as the images are being viewed. Once the report is complete and the radiologist observes the procedure level viewed indicator (indicating all images of the procedure were accessed and inferably viewed) associated with the imaging procedure, the images and report are signed off and the radiologist moves on to the next case to be read.

In another example of operation, multiple image series are generated. This is most common in the use of CT (computed tomography) and MR (magnetic resonance) modalities. In some of these procedures it is possible to have 84 series of 30 to 100 images each, for example. In this case, a viewed indicator is seen on an image series level so that the radiologist knows that all of the images of the image series have been viewed without have to go image by image through the series. The viewed indicator is placed on a series level tab of a navigation image window. A documentation processor records data in the log file indicating generated viewed indicators are associated with the viewed images series. The log file record is stored together with data representing the viewed image series as a DICOM object in repository 235 (FIG. 2). The system administrator is able to access and retrieve objects stored in repository 235 for presentation or review and may record the object on a CD or print the object using any text printer. A PACS-RIS Viewer application in system 40 is used to access a log file in order to reconstruct an imaging report preparation process. The right to edit the created image files and access the log file records containing the generated viewed indicators is restricted to prevent unauthorized manipulation of the data.

Figure 3:
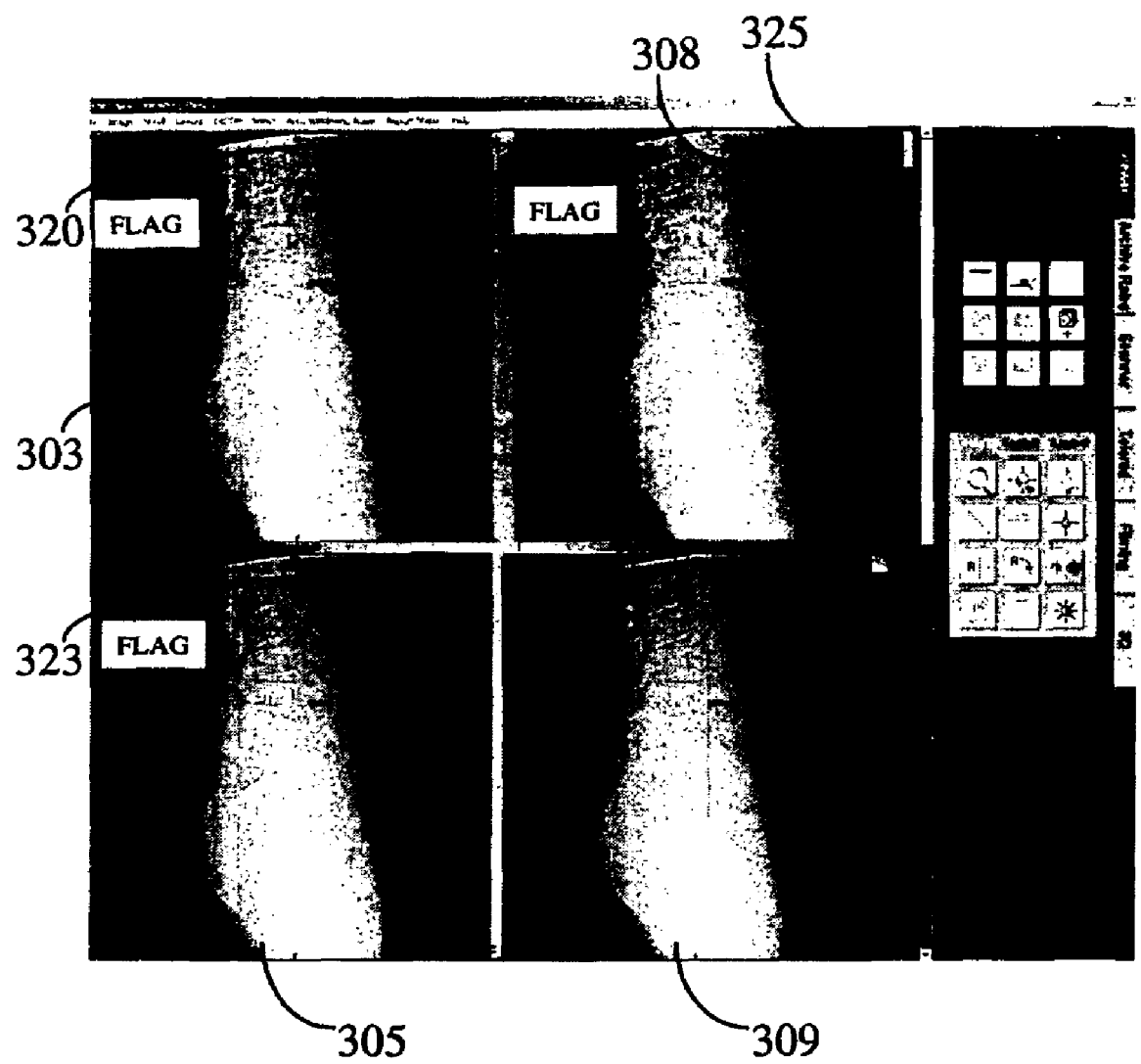
FIG. 3 shows medical images incorporating indicators, according to invention principles.

FIG. 3 illustrates medical images incorporating viewed indicators generated by system 40 (FIG. 1) in response to a physician responsible for imaging report preparation and sign-off reviewing images 303, 305 and 308 to create the report. The generated viewed indicators 320, 323 and 325 (that is the displayed "i" icon or text) show that images 303, 305 and 308 were used to create the report. FIG. 3 shows that image 309 was not taken into account by the reporting physician. System 40 provides documentation and visual indicators identifying images that are analyzed or not analyzed by a radiologist, for example, and ensures this documentation is not manipulated without creation of evidentiary data recording the manipulation using flags and Log files.

Figure 4:
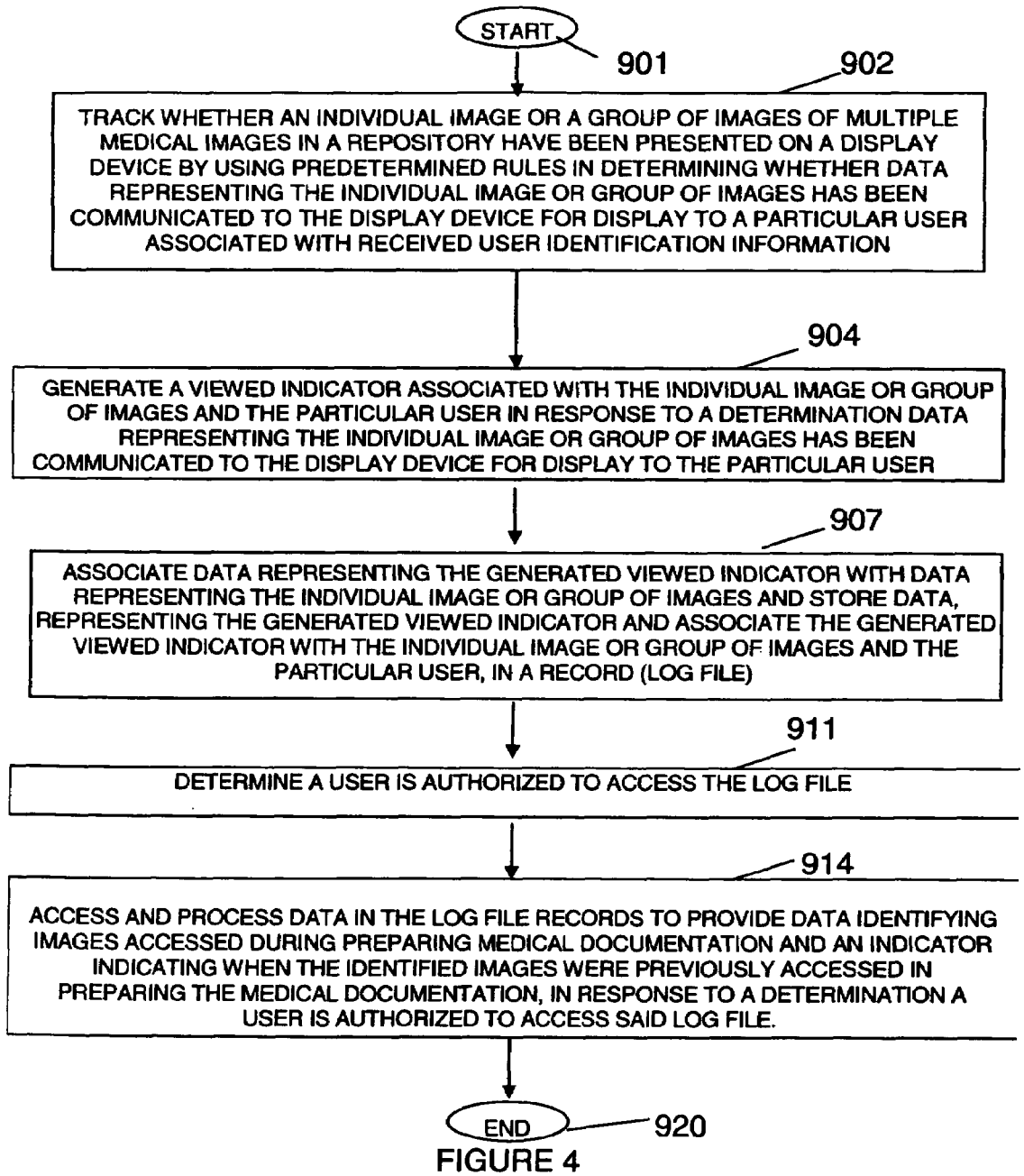
FIG. 4 shows a flowchart of a process employed by an image usage tracking and documentation system, according to invention principles.

FIG. 4 shows a flowchart of a process employed by image usage tracking and documentation system 40. In step 902 following the start at step 901, system 40 tracks whether an individual image or group of images of multiple medical images of a particular patient have been presented on workstation 12. System 40 uses predetermined rules in determining whether data representing the individual image or group of images have been communicated to workstation 12 for display to a particular user associated with received user identification information. The group of images of the particular patient comprise images related to a medical procedure or a series of images available for use in preparing medical documentation. The predetermined rules and medical images may be accessed from memory 32, repository 46, or database 14, for example. The predetermined rules determine data representing an individual image has been communicated to workstation 12 for display to a particular user in response to one or more of, a duration of time the individual image has been viewable on workstation 12, the proportion of data representing the individual image that has been communicated to workstation 12 for display, data indicating the individual image has been selected by the particular user and data indicating the individual image has been updated by the particular user. The predetermined rules also determine data representing multiple medical images has been communicated to workstation 12 for display to a particular user in response to at least one of, the number of the multiple medical images that have been communicated to workstation 12 for display to the particular user and a determination all of the multiple medical images have been communicated to workstation 12 for display to the particular user.

In addition, system 40 tracks whether an individual image of the multiple medical images is accessed during a particular documentation generation session and associates data representing the generated viewed indicator to data identifying the particular documentation generation session. In step 904 system 40 generates a viewed indicator associated with the individual image or group of images and the particular user in response to a determination data representing the individual image or group of images has been communicated to workstation 12 for display to the particular user. In one embodiment, system 40 generates a viewed indicator associated with a group of medical images and the particular user in response to a determination viewed indicators associated with corresponding individual images of the group have been generated. A report generator in step 40 automatically uses the data representing the viewed indicator in entering data in medical documentation comprising a report identifying data representing the individual display image or group of images has been communicated to workstation 12 for display to the particular user.

System 40 in step 907 associates data representing the generated viewed indicator with data representing the individual image or group of images and stores data, representing the generated viewed indicator and associating the generated viewed indicator with the individual image or group of images and the particular user, in a record (log file). In step 911 system 40 determines a user is authorized to access the log file. System 40 in step 914 accesses and processes data in the log file records to provide data identifying images accessed during preparing medical documentation and an indicator indicating when the identified images were previously accessed in preparing the medical documentation, in response to a determination a user is authorized to access the log file. The log file also contains records associating data representing generated viewed indicators with medical data of the particular patient. The indicator indicating when the identified images were previously accessed in preparing the medical documentation comprises at least one of, (a) a time and (b) a date. The process of FIG. 4 terminates at step 920.

In the FIG. 1 system, server device 18 may be implemented as a personal computer or a workstation. Database 38 provides a location for storing patient treatment records and other patient records (e.g., financial records) as well as a log file and rules repositories and data storage unit 14 provides an alternate store for these records, as well as other information in system 10. The information in data storage unit 14, database 38, unit 36 and system 40 is accessed by multiple users from multiple client devices. Patient records in data storage unit 14 include information related to a patient including, without limitation, biographical, financial, clinical, workflow, care plan and patient encounter (visit) related information.

The first local area network (LAN) 16 (FIG. 1) provides a communication network among the client device 12, the data storage unit 14 and the server device 18. The second local area network (LAN) 20 provides a communication network between the server device 18 and repositories 22. The first LAN 16 and the second LAN 20 may be the same or different LANs, depending on the particular network configuration and the particular communication protocols implemented. Alternatively, one or both of the first LAN 16 and the second LAN 20 may be implemented as a wide area network (WAN).

The communication paths 52, 56, 60, 62, 64, 66, 68 and 70 permit the various elements, shown in FIG. 1, to communicate with the first LAN 16 or the second LAN 20. Each of the communication paths 52, 56, 60, 62, 64, 66, 68 and 70 are preferably adapted to use one or more data formats, otherwise called protocols, depending on the type and/or configuration of the various elements in the Radiology information systems 10. Examples of the information system data formats include, without limitation, an RS232 protocol, an Ethernet protocol, a Medical Interface Bus (MIB) compatible protocol, DICOM protocol, an Internet Protocol (I.P.) data format, a local area network (LAN) protocol, a wide area network (WAN) protocol, an IEEE bus compatible protocol, and a Health level Seven (HL7) protocol.

The system, user interface image and processes presented in FIGS. 1-4 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, any of the functions provided by the systems of FIGS. 1 and 2 and process of FIG. 4 may be implemented in hardware, software or a combination of both. The tracking and documentation system identifies, flags and tracks not just images but other patient specific medical data read and analyzed by a physician to create a report, for example.

What is claimed is:

1. A computer implemented system for tracking medical image viewing by a user, comprising:
at least one repository storing data representing a plurality of medical images of a particular patient available for use in preparing medical documentation;
a viewing processor, coupled to said at least one repository, conditioned for automatically, tracking whether an individual image of said plurality of medical images has been presented on a display device by using predetermined rules in determining whether data representing said individual image has been communicated to said display device for display to a particular user associated with received user identification information, said predetermined rules determine data representing said individual image has been communicated to said display device for display to a particular user in response to the proportion of data, representing a portion and less than all of said individual image that has been communicated to said display device for display, exceeds a predetermined proportion and a predetermined portion less than a full size image is substantially displayed and generating a viewed indicator associated with said individual image and said particular user in response to a determination data representing said individual image has been communicated to said display device for display to said particular user; and a documentation processor, coupled to said viewing processor, conditioned for associating data representing the generated viewed indicator with data representing said individual image and storing data, representing said generated viewed indicator and associating said generated viewed indicator with said individual image and said particular user, in a record.

2. A system according to claim 1, wherein said viewing processor determines the proportion of data exceeds said predetermined proportion based on number of downloaded bytes as a proportion of total number of bytes comprising said individual image and including a report generator for automatically using said data representing said viewed indicator in entering data in a report identifying data representing said individual display image has been communicated to a display device for display to said particular user.

3. A system according to claim 1, wherein said viewing processor determines data representing said individual image has been communicated to said display device in response to determining said individual image has been presented on a display with a predetermined minimum resolution and for more than a predetermined amount of time and said predetermined rules determine data representing said individual image has been communicated to said display device for display to a particular user in response to data indicating said individual image has been selected by said particular user.

4. A system according to claim 1, wherein said plurality of medical images of said particular patient comprise at least one of, (a) images related to a medical procedure and (b) a series of images available for use in preparing medical documentation.

5. A system according to claim 1, wherein said viewing processor tracks whether an individual image of said plurality of medical images is accessed during a particular documentation generation session and said documentation processor associates data representing said generated viewed indicator to data identifying said particular documentation generation session.

6. A system according to claim 1, wherein said record comprises a log file and said log file associates an identifier identifying a series of images with an imaging examination report.

7. A system according to claim 1, wherein said predetermined rules determine data representing said individual image has been communicated to said display device for display to a particular user in response to data indicating the proportion of data representing said individual image that has been communicated to said display device for display.

8. A system according to claim 1, wherein said medical documentation comprises a medical report and said viewing processor tracks whether a series of images comprising said plurality of medical images has been presented on said display device by generating a viewed indicator associated with said series of images and said particular user in response to a determination data representing said series of images has been communicated to said display device for display to said particular user.

9. A computer implemented system for tracking medical image viewing by a user, comprising:

at least one repository storing data representing a plurality of medical images of a particular patient available for use in preparing medical documentation;

a viewing processor, coupled to said at least one repository, conditioned for automatically, tracking whether said plurality of medical images have been presented on a display device by using predetermined rules in determining whether data representing said plurality of medical images has been communicated to said display device for display to a particular user associated with received user identification information, said predetermined rules determine data representing said plurality of medical images has been communicated to said display device for display to a particular user in response to a determination a predetermined portion and less than all of said plurality of medical images have been communicated to said display device for display to said particular user and a predetermined portion less than a full size individual image is substantially displayed and generating a viewed indicator associated with said plurality of medical images and said particular user in response to a determination data representing said plurality of medical images has been communicated to said display device for display to said particular user; and a documentation processor, coupled to said viewing processor, conditioned for associating data representing the generated viewed indicator with data representing said plurality of medical images and storing data, representing said generated viewed indicator and associating said viewed indicator with said plurality of medical images and said particular user, in a record.

10. A system according to claim 9, wherein said plurality of medical images of said particular patient comprise at least one of, (a) images related to a medical procedure and (b) a series of images available for use in preparing medical documentation and said viewing processor tracks whether a series of images comprising said plurality of medical images has been presented on said display device by generating a viewed indicator associated with said series of images and said particular user in response to a determination data representing said series of images has been communicated to said display device for display to said particular user.

11. A system according to claim 9, wherein said predetermined rules determine data representing said plurality of medical images has been communicated to said display device for display to a particular user in response to the number of said plurality of medical images that have been communicated to said display device for display to said particular user and said viewing processor determines said predetermined portion and less than all of said plurality of medical images have been communicated to said display device for display to said particular user in response to determining said predetermined portion and less than all of said plurality of medical images have been presented on a display with a predetermined minimum resolution for more than a predetermined amount of time.

12. A system according to claim 9, wherein said viewing processor determines a predetermined portion and less than all of said plurality of medical images have been communicated to said display device based on number of downloaded bytes as a proportion of total number of bytes comprising said plurality of medical images.

13. A system according to claim 12, wherein said viewing processor generates said viewed indicator associated with said plurality of medical images and said particular user in response to a determination a viewed indicator has been generated for individual images of said plurality of medical images.

14. A system according to claim 13, wherein said viewing processor generates said viewed indicator associated with said plurality of medical images in response to a determination a viewed indicator associated with an individual image has been generated for a predetermined proportion of said plurality of medical images.

15. A computer implemented system for indicating medical data previously accessed by a healthcare worker in preparing medical documentation, comprising:

a stored log file containing records associating data representing generated viewed indicators with data representing corresponding medical images of a particular patient and with an identifier of a particular user, an individual generated viewed indicator indicating an associated corresponding image was accessed by said particular user in preparing medical documentation, a generated viewed indicator being generated in response to predetermined rules determining data representing said corresponding image has been communicated to a display device for display to said particular user in response to, (a) a duration of time said corresponding image has been viewable on said display device and (b) the proportion of data, representing a portion and less than all of said corresponding image that has been communicated to said display device for display, exceeds a predetermined proportion and a predetermined portion less than a full size image is substantially displayed;

an authorization processor conditioned for determining a user is authorized to access said log file; and a data processor, coupled to said authorization processor, conditioned for accessing and processing data in said log file records to provide data identifying images accessed during preparing medical documentation and an indicator indicating when the identified images were previously accessed in preparing said medical documentation, in response to a determination a user is authorized to access said log file.

16. A system according to claim 15, wherein said log file contains records associating data representing generated viewed indicators with medical data of said particular patient and said log file associates an identifier identifying a series of images with an imaging examination report.

17. A system according to claim 15, wherein said indicator indicating when said identified images were previously accessed in preparing said medical documentation comprises at least one of, (a) a time and (b) a date.

* * * * *